United States Patent
Koch et al.

[11] Patent Number: 6,103,532
[45] Date of Patent: Aug. 15, 2000

[54] VAPOR RECOVERY SYSTEM UTILIZING A FIBER-OPTIC SENSOR TO DETECT HYDROCARBON EMISSIONS

[75] Inventors: Wolfgang H. Koch, Batavia; Arthur R. Brown, Warrenville, both of Ill.

[73] Assignee: Tokheim Corporation, Fort Wayne, Ind.

[21] Appl. No.: 09/134,858

[22] Filed: Aug. 14, 1998

[51] Int. Cl.[7] .................................................. G01N 21/59
[52] U.S. Cl. ........................... 436/55; 436/143; 436/167; 422/62; 422/82.09; 422/91; 422/110; 141/7; 141/83
[58] Field of Search ..................... 422/82.09, 91, 422/108, 110, 62; 436/143, 164, 165, 167, 55; 141/7, 83, 95, 96; 250/227.16; 356/437

[56] References Cited

U.S. PATENT DOCUMENTS

| | | |
|---|---|---|
| 4,050,895 | 9/1977 | Hardy et al. . |
| 4,503,994 | 3/1985 | Pyle . |
| 4,590,462 | 5/1986 | Moorehead . |
| 4,764,343 | 8/1988 | Nyberg . |
| 4,882,499 | 11/1989 | Luukkala et al. . |
| 4,931,851 | 6/1990 | Sibbald et al. . |
| 5,015,099 | 5/1991 | Nagai et al. . |
| 5,015,843 | 5/1991 | Seitz et al. . |
| 5,039,855 | 8/1991 | Kemeny et al. . |
| 5,084,614 | 1/1992 | Berkner . |
| 5,138,153 | 8/1992 | Gergely et al. . |
| 5,168,156 | 12/1992 | Fischer et al. . |
| 5,187,366 | 2/1993 | Hopenfeld . |
| 5,280,172 | 1/1994 | Di Bin et al. . |
| 5,330,073 | 7/1994 | Collins et al. . |
| 5,343,037 | 8/1994 | Berkcan . |
| 5,378,889 | 1/1995 | Lawrence . |
| 5,417,256 | 5/1995 | Hartsell, Jr. et al. ........................ 141/7 |
| 5,422,495 | 6/1995 | Cohn . |
| 5,507,325 | 4/1996 | Finlayson ................................. 141/83 |

Primary Examiner—Jeffrey Snay
Attorney, Agent, or Firm—Randall J. Knuth

[57] ABSTRACT

A method and apparatus is disclosed for sensing hydrocarbon in the vapor path of fuel dispensers using a fiber-optic sensor. The sensor includes an absorber-expander sensing structure mechanically coupled to the fiber body and responsive to the presence of effluent fuel components for absorbing the hydrocarbon therein and expanding in response thereto. The expansion activity has the effect of generating a microbend deformation in the fiber, producing detectable changes in the optical throughput representing the concentration of hydrocarbon that is sensed by the absorber-expander element. The fiber-optic sensor is particularly useful in a vapor recovery system by providing an optical signal that is representative of the ambient hydrocarbon concentration. The concentration level of hydrocarbon represented by the detected change in fiber transmittance serves as the basis for regulating the rate at which the vapor pump collects effluent vapors discharged during refueling, namely by appropriately adjusting the vapor pump operating speed.

83 Claims, 5 Drawing Sheets

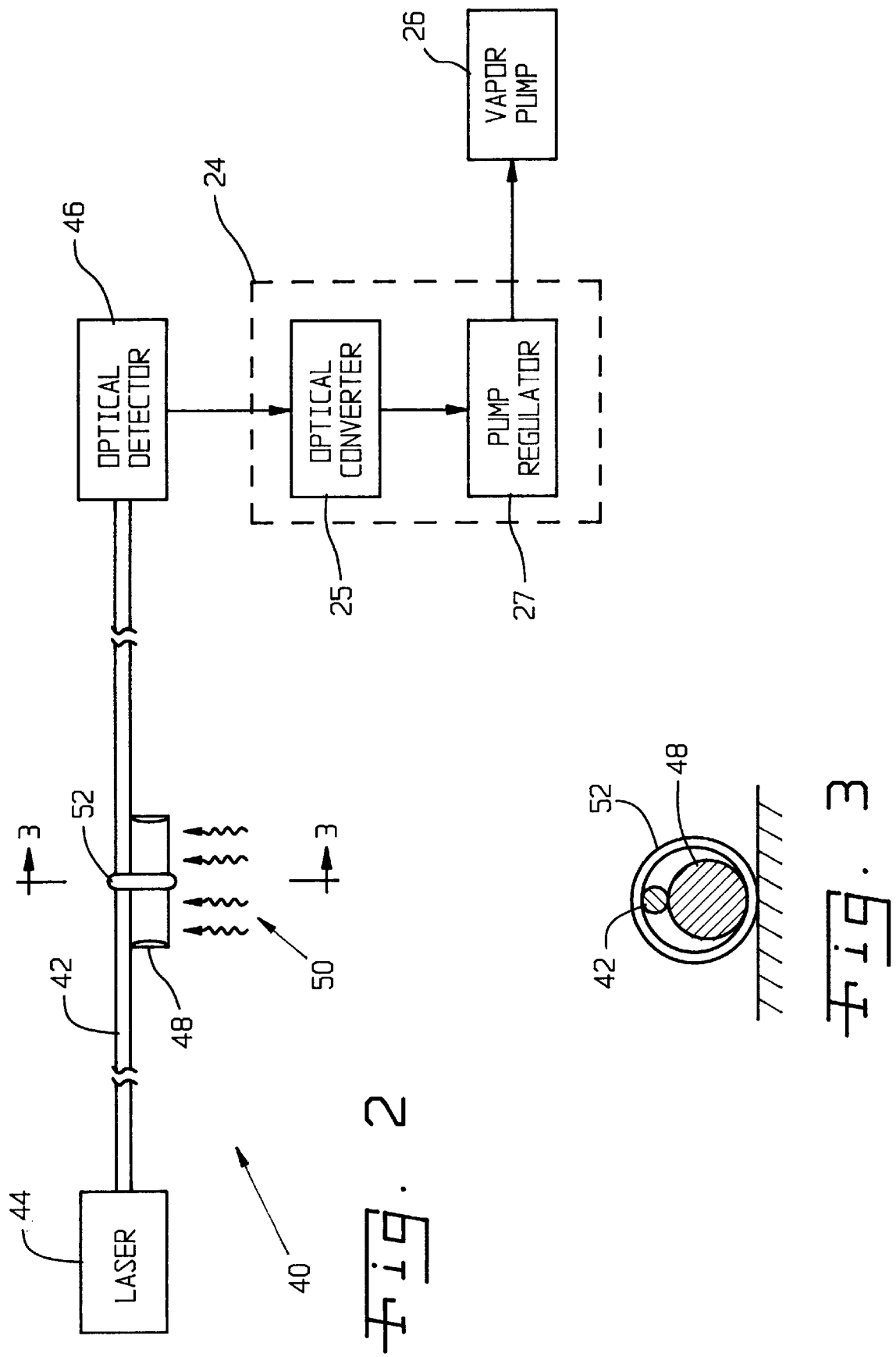

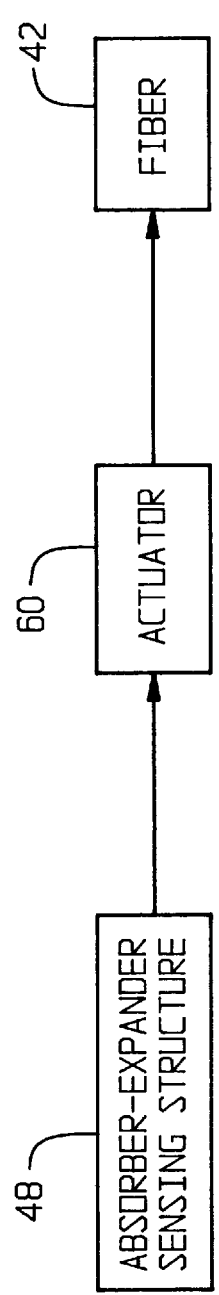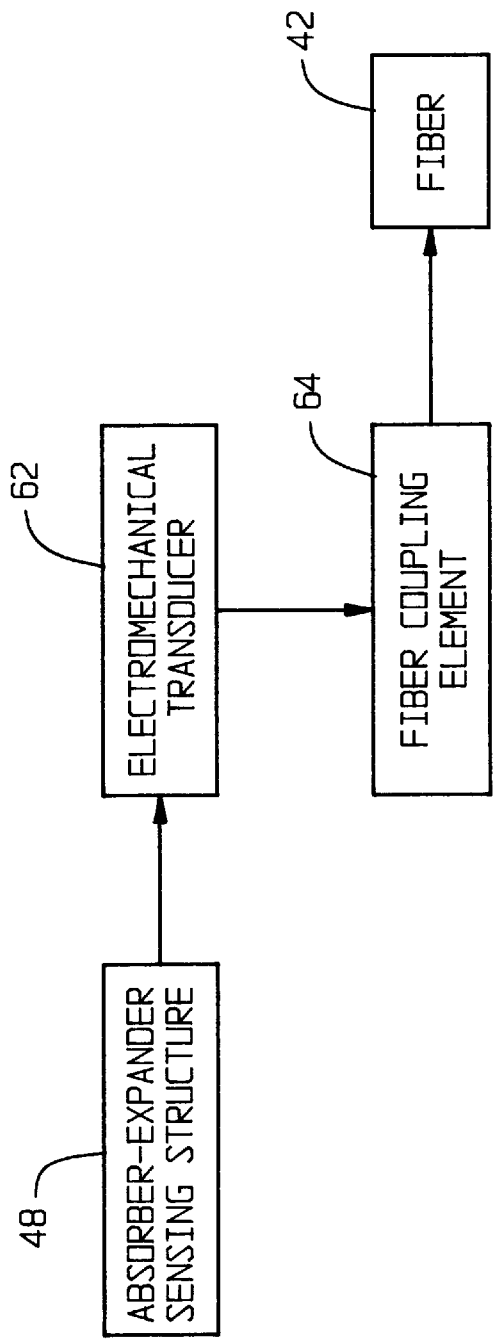

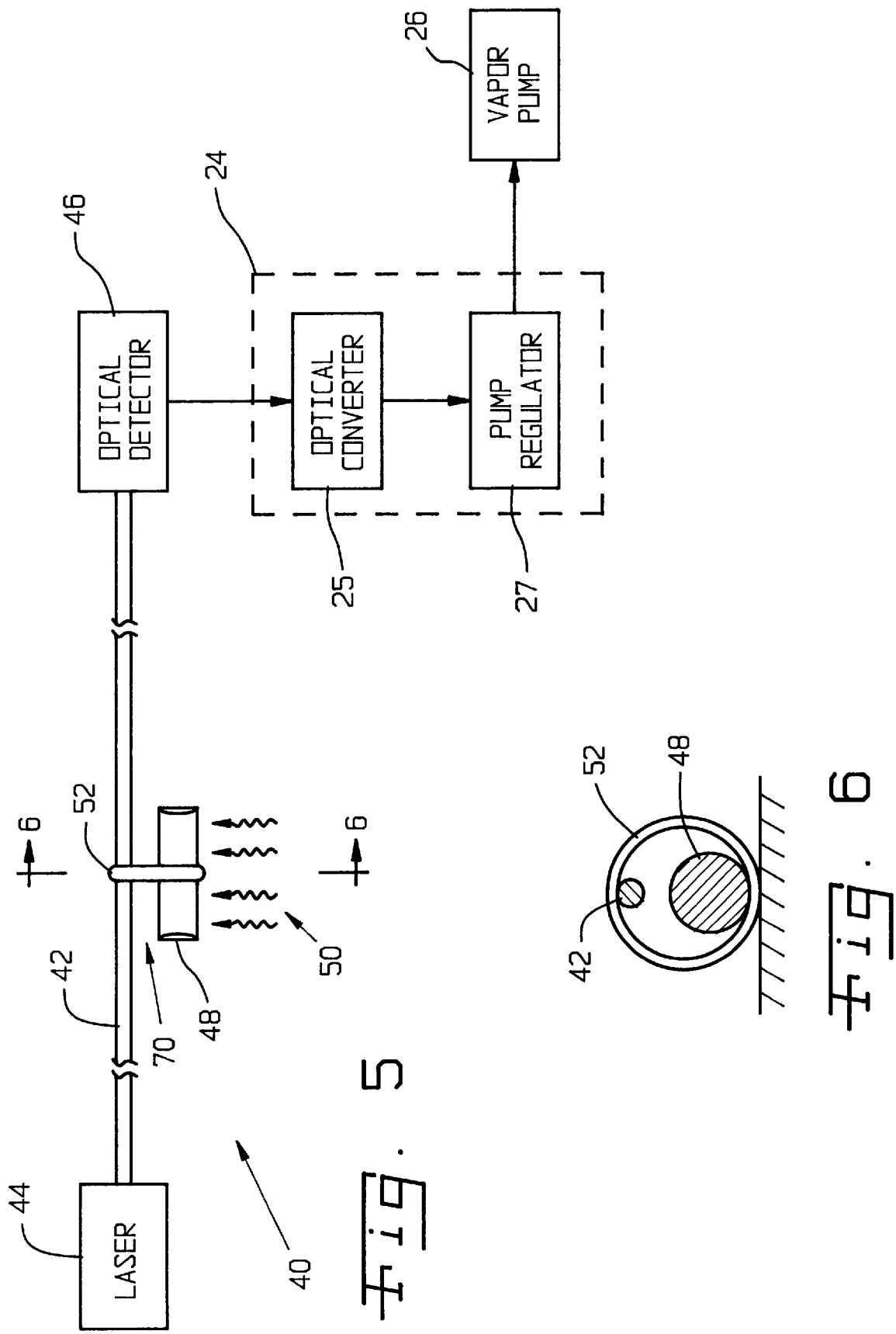

VAPOR RECOVERY SYSTEM UTILIZING A FIBER-OPTIC SENSOR TO DETECT HYDROCARBON EMISSIONS

BACKGROUND OF THE INVENTION

1. Field of the invention

The present invention generally relates to vapor recovery apparatus for use in fuel dispenser applications, and, more particularly, to method and apparatus for detecting hydrocarbon emissions discharged during refueling activity using a fiber-optic sensor and for regulating the vapor pump based on the sensed hydrocarbon concentration.

2. Description of the related art

As gasoline or other fuel is dispensed into an automobile or other motor vehicle from a fuel delivery system, the incoming fuel displaces volatilized fuel vapors and forces their discharge from the containment tank. These vapors must be captured or otherwise collected to prevent their escape and contamination of the surrounding environment. Vacuum-assisted stage II vapor recovery systems serve to recover hydrocarbon vapors displaced from vehicle fuel tanks during fuel dispensing operations. The released vapors are collected by using a vapor pump to draw vapors into the vapor recovery system for subsequent storage, recycling or destruction. The rate at which vapor is collected is controlled by varying the speed of the vapor pump. For maximum performance and efficiency of the vapor recovery system, the speed of the vapor pump must be adequately controlled so that vapor is collected at a rate that corresponds as closely as possible to the instantaneous rate of effluent vapor discharge that is developed during a refueling operation, while minimizing the retrieval of oxygen.

The challenge encountered by all such vacuum-assisted vapor recovery systems is finding a suitable vapor monitoring system capable of dynamically sensing the presence of hydrocarbon components and generating a signal that accurately measures the detected hydrocarbon. One limitation experienced by conventional detection apparatus involves an inability to sense hydrocarbon in both its vapor state and liquid state. This deficiency is most pronounced when the refueling operation occurs during temperature and pressure conditions favorable to the condensation of gaseous hydrocarbon. The absence of any capability to adequately remove the hydrocarbon condensate leads to false readings and an overall corruption of the sensing measurement data, resulting in an unreliable control mechanism for regulating the vapor pump.

It is also critical to proper functioning of the vapor recovery system that the vapor sensing element be highly sensitive to the presence of hydrocarbon. Otherwise, if low levels of hydrocarbon concentration fall below a threshold point at which the sensing element becomes incapable of registering the presence of hydrocarbon, the vapor pump will be directed to continue in operation at its current speed corresponding to the registration of a prior level of hydrocarbon detection that is no longer valid. This undetected condition may lead to excessive collection of oxygen components due to the mismatch between the vapor pump operating speed and the actual but undetected hydrocarbon concentration.

SUMMARY OF THE INVENTION

The invention comprises, in one form thereof, a method and apparatus for sensing hydrocarbon in the vapor path of fuel dispensers using a fiber-optic sensor. The sensor includes, in one form thereof, an absorber-expander sensing structure mechanically coupled to the fiber body and responsive to the presence of effluent fuel components for absorbing the hydrocarbon therein and expanding in response thereto. The expansion activity has the effect of generating a microbend deformation in the fiber, producing detectable changes in the optical throughput representing the concentration of hydrocarbon that is sensed by the absorber-expander element. The fiber-optic sensor is particularly useful in a vapor recovery system by providing an optical signal that is representative of the ambient hydrocarbon concentration. The concentration level of hydrocarbon represented by the detected change in fiber transmittance serves as the basis for regulating the rate at which the vapor pump collects effluent vapors discharged during refueling, namely by appropriately adjusting the vapor pump operating speed.

The invention comprises, in another form thereof, a system for recovering hydrocarbon effluents from a container for use with a fuel delivery system. The system includes a communication means for conveying electromagnetic energy, a transmitter means for introducing electromagnetic energy into the communication means, and a receiver means for detecting electromagnetic energy propagating through the communication means. A sensor means, disposed in effluent-detecting relationship to the container, is provided for sufficiently engaging the communication means in response to the presence of hydrocarbon effluents sensed by the sensor means, to induce a change in the transmittance thereof. There is further provided a vapor collection means for controllably collecting the hydrocarbon effluents from the container, and a regulator means for controlling the rate of effluent collection by the vapor collection means in accordance with the level of energy detected by the receiver means. The sensor means is preferably disposed in a vapor recovery pathway.

The system further includes a thermal applicator means, disposed in heat-exchange relationship to the sensor means, for applying thermal energy to the sensor means to promote removal of hydrocarbon liquid therefrom. In one form of the system, the communication means includes an optical fiber, the transmitter means includes a laser, and the receiver means includes an optical detector. Engagement of the communication means by the sensor means effects, in one form thereof, a microbending of the optical fiber. The vapor collection means includes, in one form thereof, a vapor pump. The regulator means further includes, in one form thereof, a conversion means for converting the energy detected by the receiver means into a vapor control signal representative of the concentration of hydrocarbon sensed by the sensor means and represented by the change in transmittance of the communication means; and means for applying the vapor control signal provided by the conversion means to the vapor pump to effect control thereof.

The communication means includes, in one form thereof, an optical fiber. The sensor means includes, in one form thereof, a sensing structure, mechanically coupled to at least a portion of the optical fiber and reactively sensitive to the presence of hydrocarbon in at least one of a liquid state and a vapor state, for absorbing hydrocarbon upon the presence thereof and expanding in response thereto. The expansion of the sensing structure effects a microbending of the optical fiber. The sensing structure is characterized such that the absorption of hydrocarbon therein and the expansion thereof in response to the absorption is repeatedly substantially reversible. The sensing structure is preferably formed, at least in part, of a red silicone rubber member. A thermal applicator means is provided for controllably applying thermal energy to the sensing structure to promote hydrocarbon desorption therein and effect contraction thereof from a hydrocarbon-induced expansive state. The sensor means includes, in another form thereof, a plurality of sensing structures disposed in relative spaced-apart relationship along the optical fiber and mechanically coupled thereto, each of the plurality of sensing structures being reactively sensitive to the presence of hydrocarbon in at least one of a liquid state and a vapor state for absorbing hydrocarbon upon the presence thereof and expanding in response thereto.

The communication means includes, in another form thereof, a plurality of optical fiber sections arranged in seriatim and each disposed in light-communicative relationship with any adjacent ones of the plural optical fiber sections and displaced relative to the adjacent optical fiber sections by a coupling region therebetween. The sensor means includes, in one form thereof, a sensing structure, mechanically coupled to at least a portion of one of the plural optical fiber sections and reactively sensitive to the presence of hydrocarbon in at least one of a liquid state and a vapor state, for absorbing hydrocarbon upon the presence thereof and expanding in response thereto. The expansion activity of the sensing structure effects, in one form thereof, a microbending of the one optical fiber section; and effects, in another form thereof, a relative transverse displacement between the one optical fiber section and others of the optical fiber sections adjacent thereto. The sensing structure is characterized such that the absorption of hydrocarbon therein and the expansion thereof in response to the absorption is repeatedly substantially reversible. The sensing structure is preferably formed, at least in part, of a red silicone rubber member. A thermal applicator means is provided for controllably applying thermal energy to the sensing structure to promote hydrocarbon desorption therein and effect contraction thereof from a hydrocarbon-induced expansive state.

The invention comprises, in another form thereof, a system for recovering hydrocarbon effluents from a container for use with a fuel delivery system. The system includes a communication means for conveying electromagnetic energy, a transmission means for introducing electromagnetic energy into the communication means, and a receiver means for detecting electromagnetic energy propagating through the communication means. There is further provided a sensor means, disposed in effluent-sensing relationship to the container and further disposed in spaced-apart relation to the communication means, for engaging the communication means in response to the presence of hydrocarbon effluents sensed by the sensor means to induce a change in the transmittance thereof. A vapor collection means is provided for controllably collecting the hydrocarbon effluents from the container. A regulator means, operatively coupled to the receiver means, is provided for controlling the rate of effluent collection by the vapor collection means in accordance with the level of energy detected by the receiver means. The sensor means is preferably disposed in a vapor recovery pathway.

The system further includes a thermal applicator means, disposed in heat-exchange relationship to the sensor means, for applying thermal energy to the sensor means to promote removal of hydrocarbon liquid therefrom. In one form of the system, the communication means includes an optical fiber, the transmitter means includes a laser, and the receiver means includes an optical detector. The engagement of the communication means by the sensor means effects a microbending of the optical fiber. The vapor collection means includes, in one form thereof, a vapor pump. The regulator means further includes, in one form thereof, a conversion means for converting the energy detected by the receiver means into a vapor control signal representative of the concentration of hydrocarbon sensed by the sensor means and represented by the change in transmittance of the communication means; and means for applying the vapor control signal provided by the conversion means to the vapor pump to effect control thereof.

The communication means includes, in one form thereof, an optical fiber. The sensor means includes, in one form thereof, a sensing structure, disposed in spaced-apart relation to the optical fiber and reactively sensitive to the presence of hydrocarbon in at least one of a liquid state and a vapor state, for absorbing hydrocarbon upon the presence thereof and expanding in response thereto sufficient to bring the sensing structure into engagement with the optical fiber. The expansion activity of the sensing structure effects a microbending of the optical fiber. The sensing structure is characterized such that the absorption of hydrocarbon therein and the expansion thereof in response to the absorption is repeatedly substantially reversible. The sensing structure is preferably formed, at least in part, of a red silicone rubber member. A thermal applicator means is provided for controllably applying thermal energy to the sensing structure to promote hydrocarbon desorption therein and effect contraction thereof from a hydrocarbon-induced expansive state.

The sensor means includes, in another form thereof, a plurality of sensing structures disposed in relative spaced-apart relationship along the optical fiber and each spaced-apart therefrom, each of the plurality of sensing structures being reactively sensitive to the presence of hydrocarbon in at least one of a liquid state and a vapor state for absorbing hydrocarbon upon the presence thereof and expanding in response thereto sufficient to cause at least one of the plurality of sensing structures to be brought into engagement with the optical fiber.

The sensor means includes, in yet another form thereof, a sensing structure, which is reactively sensitive to the presence of hydrocarbon in at least one of a liquid state and a vapor state, for absorbing hydrocarbon upon the presence thereof and expanding in response thereto; and an actuator means, disposed relative to the sensing structure for detection of the expansion thereof, for engaging the optical fiber in response to and in accordance with the detected expansion. The engagement of the optical fiber by the actuator means effects a microbending of the optical fiber. The sensing structure is characterized such that the absorption of hydrocarbon therein and the expansion thereof in response to the absorption is repeatedly substantially reversible. The sensing structure is preferably formed, at least in part, of a red silicone rubber member. A thermal applicator means is provided for controllably applying thermal energy to the sensing structure to promote hydrocarbon desorption therein and effect contraction thereof from a hydrocarbon-induced expansive state.

The reliability of the sensor apparatus in generating continuous and reproducible responses to the presence of hydrocarbon is attributable not only to the reversible performance of the absorber-expander element during its expansion-contraction cycles, but is further enhanced by the elastic quality of the optical fiber. the amount of microbending in the fiber body begins to diminish and eventually disappears as the absorber-expander element experiences a disassociative process involving the hydrocarbon molecules and undergoes a physical contraction from its hydrocarbon-induced expansive state. A progressive reduction in the deformation of the fiber occurs simultaneously with desorption of the detected hydrocarbon because the elasticity of the fiber body allows it to return to its original formation as the deforming stimulus (i.t., the absorber-expander element in its expanded state) disengages from intimate contact with the fiber. the optical transmittance of the fiber under static conditions (i.e., absence of hydrocarbon) is thereby substantially unaffected by any previous microbend activity therein. In essence, the fiber possesses no memory characteristic capable of retaining any traces, either structurally or otherwise, of its operational history. This same attribute is also applicable to the entire sensor apparatus since the absorber-expander element likewise demonstrates no retention of any prior expansion-contraction activity.

The sensor means includes, in yet another form thereof, a sensing structure, which is reactively sensitive to the presence of hydrocarbon in at least one of a liquid state and a vapor state, for absorbing hydrocarbon upon the presence thereof and expanding in response thereto; an electromechanical sensor for detecting the expansion of the sensing structure and converting the detected expansion into an electrical signal representative thereof; and means for engaging the optical fiber in response to and in accordance with the electrical signal provided by the electromechanical sensor.

The communication means includes, in another form thereof, a plurality of optical fiber sections arranged in seriatim and each disposed in light-communicative relationship with any adjacent ones of the plural optical fiber sections and displaced relative to the adjacent optical fiber sections by a coupling region therebetween. The sensor means includes, in one form thereof, a sensing structure, disposed in spaced-apart relation to one of the plural optical fiber sections and reactively sensitive to the presence of hydrocarbon in at least one of a liquid state and a vapor state, for absorbing hydrocarbon upon the presence thereof and expanding in response thereto sufficient to bring the sensing structure into engagement with the one optical fiber section. The engagement of the one optical fiber section by the sensing structure during expansion thereof effects, in one form thereof, a microbending of the one optical fiber section; and effects, in another form thereof, a relative transverse displacement between the one optical fiber section and others of the optical fiber sections adjacent thereto. The sensing structure is characterized such that the absorption of hydrocarbon therein and the expansion thereof in response to the absorption is repeatedly substantially reversible. The sensing structure is preferably formed, at least in part, of a red silicone rubber member. A thermal applicator means is provided for controllably applying thermal energy to the sensing structure to promote hydrocarbon desorption therein and effect contraction thereof from a hydrocarbon-induced expansive state.

The sensor means includes, in another form thereof, a sensing structure, which is reactively sensitive to the presence of hydrocarbon in at least one of a liquid state and a vapor state, for absorbing hydrocarbon upon the presence thereof and expanding in response thereto; and an actuator means, disposed relative to the sensing structure for detection of the expansion thereof, for engaging one of the plural optical fiber sections in response to and in accordance with the detected expansion to induce a change in transmittance of the communication means. The engagement of the one optical fiber section by the actuator means produces, in one form thereof, a microbend therein, and produces, in another form thereof, an optical misalignment of the one optical fiber section relative to others of the optical fiber sections adjacent thereto. The sensing structure is characterized such that the absorption of hydrocarbon therein and the expansion thereof in response to the absorption is repeatedly substantially reversible. The sensing structure is preferably formed, at least in part, of a red silicone rubber member. A thermal applicator means is provided for controllably applying thermal energy to the sensing structure to promote hydrocarbon desorption therein and effect contraction thereof from a hydrocarbon-induced expansive state.

The sensor means includes, in yet another form thereof, a sensing structure, which is reactively sensitive to the presence of hydrocarbon in at least one of a liquid state and a vapor state, for absorbing hydrocarbon upon the presence thereof and expanding in response thereto; an electromechanical sensor for detecting the expansion of the sensing structure and converting the detected expansion into an electrical signal representative thereof; and a means for engaging one of the optical fiber sections in response to and in accordance with the electrical signal provided by the electromechanical sensor.

The invention comprises, in yet another form thereof, a system for monitoring the presence of hydrocarbon effluents from a container, wherein the monitoring system is operatively associated with a fuel delivery system that is operative to dispense fuel into the container. The monitoring system includes a communication means for conveying electromagnetic energy, a transmitter means for introducing electromagnetic energy into the communication means, and a receiver means for detecting electromagnetic energy propagating through the communication means. There is further provided a sensor means, disposed in effluent-detecting relationship to the container, for sufficiently engaging the communication means in response to the presence of hydrocarbon effluents sensed by the sensor means to induce a change in the transmittance thereof. The sensor means is preferably disposed in a vapor recovery pathway.

The monitoring system further includes a vapor collection means for controllably collecting the hydrocarbon effluents from the container, and a regulator means for controlling the rate of effluent collection by the vapor collection means in accordance with the level of energy detected by the receiver means. The vapor collection means includes, in one form thereof, a vapor pump. The regulator means further includes a conversion means for converting the energy detected by the receiver means into a vapor control signal representative of the concentration of hydrocarbon sensed by the sensor means and represented by the change in transmittance of the communication means; and a means for applying the vapor control signal provided by the conversion means to the vapor pump to effect control thereof. A thermal applicator means, disposed in heat-exchange relationship to the sensor means, is provided for applying thermal energy to the sensor means to promote removal of hydrocarbon liquid therefrom.

The communication means includes, in one form thereof, an optical fiber. The sensor means includes, in one form thereof, a sensing structure, mechanically coupled to at least a portion of the optical fiber and reactively sensitive to the presence of hydrocarbon in at least one of a liquid state and a vapor state, for absorbing hydrocarbon upon the presence thereof and expanding in response thereto. The expansion of the sensing structure effects a microbending of the optical fiber. The sensing structure is characterized such that the absorption of hydrocarbon therein and the expansion thereof in response to the absorption is repeatedly substantially reversible. The sensing structure is preferably formed, at least in part, of a red silicone rubber member. A thermal applicator means is provided for controllably applying thermal energy to the sensing structure to promote hydrocarbon desorption therein and effect contraction thereof from a hydrocarbon-induced expansive state.

The invention comprises, in yet another form thereof, a system for monitoring the presence of hydrocarbon effluents from a container, wherein the monitoring system is operatively associated with a fuel delivery system that is operative to dispense fuel into the container. The monitoring system includes a first optical fiber and a second optical fiber disposed in reciprocal light-communicative relationship and relatively displaced at free ends thereof by a coupling region therebetween; a transmitter means for introducing electromagnetic energy into the first optical fiber; and a receiver means for detecting electromagnetic energy propagating through the second optical fiber. There is further provided a sensing structure, disposed in effluent-detecting relationship to the container and reactively sensitive to the presence of hydrocarbon in at least one of a liquid state and a vapor state, for absorbing hydrocarbon upon the presence thereof and expanding in response thereto. A light-blocking means is provided for attenuating the propagation of light incident thereon. The monitoring system further includes an actuator means, integrally coupled to the light-blocking means and disposed relative to the sensing structure for detection of the expansion thereof, for sufficiently engaging the light-blocking means in response to and in accordance with the detected expansion to reversibly interpose the light-blocking means into the coupling region between the respective free ends of the first optical fiber and the second optical fiber to induce a change in the transmittance therebetween. The sensing structure is characterized such that the absorption of hydrocarbon therein and the expansion thereof in response to the absorption is repeatedly substantially reversible. The sensing structure is preferably formed, at least in part, of a red silicone rubber member. A thermal applicator means is provided for controllably applying thermal energy to the sensing structure to promote hydrocarbon desorption therein and effect contraction thereof from a hydrocarbon-induced expansive state.

The invention comprises, in yet another form thereof, a method of recovering hydrocarbon effluents from a container for use with a fuel delivery system. The method includes the steps of providing an optical fiber, transmitting electromagnetic energy into the optical fiber, and providing a sensing structure, disposed in effluent-detecting relationship to the container, for sufficiently engaging the optical fiber in response to the presence of hydrocarbon effluents sensed by the sensing structure to induce a change in the transmittance thereof. The method further includes the steps of detecting electromagnetic energy propagating through the optical fiber, controllably collecting the hydrocarbon effluents from the container, and regulating the rate of effluent collection in accordance with the level of detected energy. The sensing structure is preferably formed, at least in part, of a red silicone rubber member. The step of applying thermal energy to the sensing structure is further provided to promote removal of hydrocarbon liquid therefrom.

The sensing structure is reactively sensitive to the presence of hydrocarbon in at least one of a liquid state and a vapor state for absorbing hydrocarbon upon the presence thereof and expanding in response thereto. The expansion of the sensing structure effects a microbending of the optical fiber. The sensing structure is characterized such that the absorption of hydrocarbon therein and the expansion thereof in response to the absorption is repeatedly substantially reversible. The step of applying thermal energy to the sensing structure promotes hydrocarbon desorption therein and effects contraction thereof from a hydrocarbon-induced expansive state.

The invention comprises, in still yet another form thereof, a method of monitoring the presence of hydrocarbon effluents from a container for use with a fuel delivery system that is operative to dispense fuel into the container. The monitoring method includes the steps of providing an optical fiber; transmitting electromagnetic energy into the optical fiber; providing a sensing structure, disposed in effluent-detecting relationship to the container, for sufficiently engaging the optical fiber in response to the presence of hydrocarbon effluents sensed by the sensing structure to induce a change in the transmittance thereof; and detecting electromagnetic energy propagating through the optical fiber. The method further includes the steps of controllably collecting the hydrocarbon effluents from the container, and regulating the rate of effluent collection in accordance with the level of detected energy.

The step of hydrocarbon effluent collection includes the step of providing a vapor pump. The sensing structure is preferably formed, at least in part, of a red silicone rubber member. The step of applying thermal energy to the sensing structure is further provided to promote removal of hydrocarbon liquid therefrom. The sensing structure is reactively sensitive to the presence of hydrocarbon in at least one of a liquid state and a vapor state for absorbing hydrocarbon upon the presence thereof and expanding in response thereto. The expansion of the sensing structure effects a microbending of the optical fiber. The sensing structure is characterized such that the absorption of hydrocarbon therein and the expansion thereof in response to the absorption is repeatedly substantially reversible. The step of applying thermal energy to the sensing structure promotes hydrocarbon desorption therein and effects contraction thereof from a hydrocarbon-induced expansive state.

One advantage of the present invention is that the absorber-expander sensing structure is capable of being heated without affecting its structural or operational integrity, permitting rapid evaporation of hydrocarbon condensate that makes it an ideal candidate for a fuel dispenser application.

Another advantage of the present invention is that the physical mechanism signifying the presence of hydrocarbon effluents, namely the absorption of hydrocarbon in the sensing structure and the accompanying expansion activity, is substantially reversible, permitting a cyclic and continuously repeatable response by the fiber-optic sensor to the presence of fuel components in the vapor recovery fuel line, which is notably accomplished without any adverse structural degradation in the absorber-expander element.

Yet another advantage of the present invention is that the absorber-expander sensing structure is capable of detecting the presence of hydrocarbon in both a liquid state and a vapor state, such that a vapor recovery system incorporating the fiber-optic sensor is suitable for use over a range of operating conditions favoring the condensation of vapor fuel emissions.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein:

FIG. 2 is a schematic block diagram view of a fiber-optic sensor apparatus configured for placement in the effluent vapor path of a fuel dispensing system, wherein the absorber-expander element is mechanically coupled to the optical fiber, according to another embodiment of the present invention;

FIG. 3 is a longitudinal view taken in cross-section depicting an integrated arrangement including the absorber-expander sensing structure and the optical fiber disclosed in the sensor apparatus of FIG. 2;

FIGS. 4A and 4B are block diagram illustrations of respective fiber-optic sensor apparatus configured for placement in the effluent vapor path of a fuel dispensing system, wherein the absorber-expander element is mechanically coupled to the optical fiber via respective coupling devices, according to further embodiments of the present invention;

FIG. 5 is a schematic block diagram view of a fiber-optic sensor apparatus configured for placement in the effluent vapor path of a fuel dispensing system, wherein the absorber-expander element is spaced-apart from the optical fiber, according to yet another embodiment of the present invention;

FIG. 6 is a longitudinal view taken in cross-section depicting an integrated arrangement including the absorber-expander sensing structure and the optical fiber disclosed in the sensor apparatus of FIG. 5.

Figure 1:
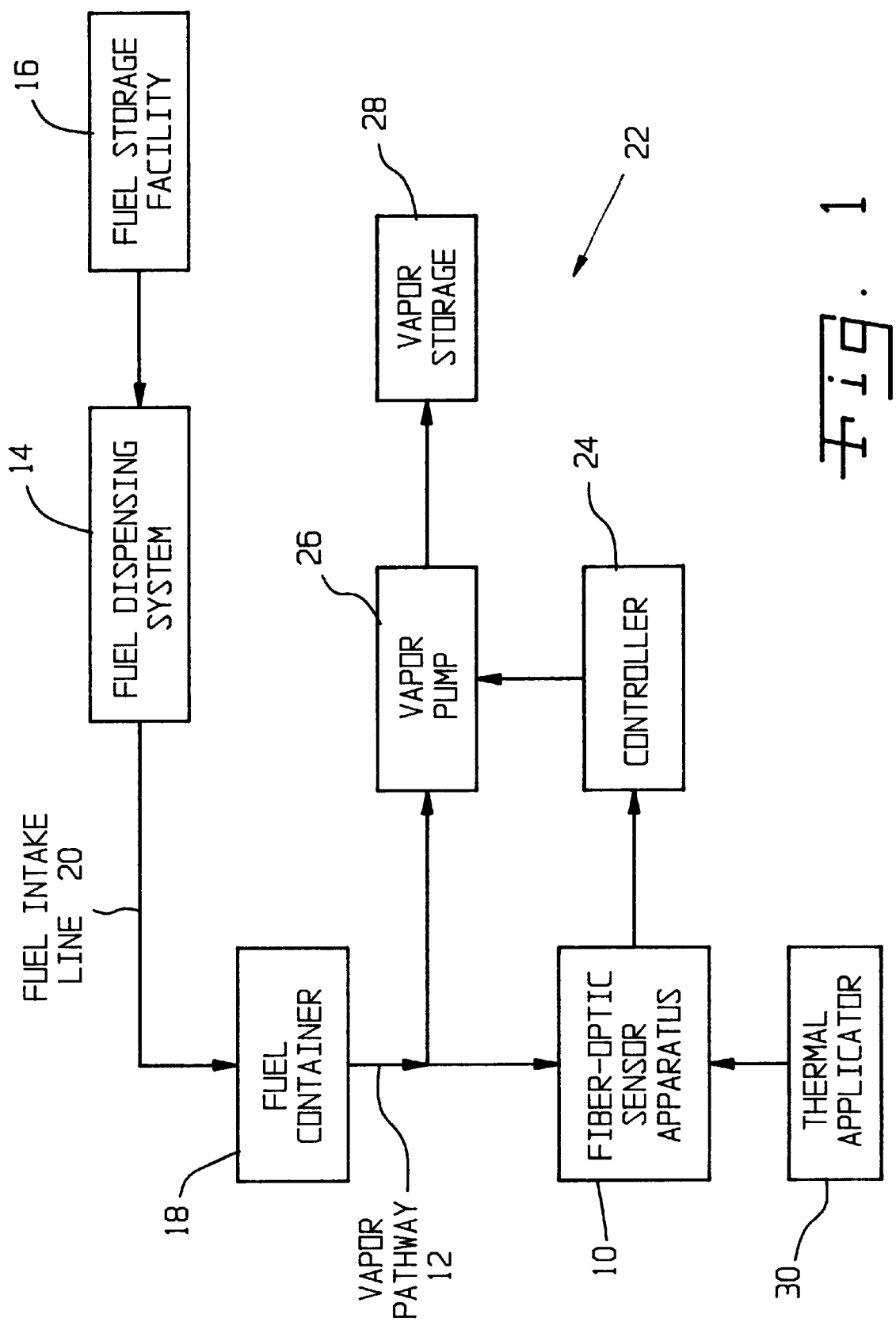
FIG. 1 is a block diagram illustration of a fiber-optic sensor apparatus integrated into the effluent vapor path of a fuel dispensing system and adapted for use with a vapor recovery system, according to one embodiment of the present invention.

Corresponding reference characters indicate corresponding parts throughout the several views. The exemplification set forth herein illustrates one preferred embodiment of the invention, in one form thereof, and such exemplification is not to be construed as limiting the scope of the invention in any manner.

DETAILED DESCRIPTION OF THE INVENTION

Referring to FIG. 1, there is shown a block diagram, according to one embodiment of the present invention, for illustrating the integration of a fiber-optic sensor apparatus 10 into vapor pathway 12 adapted for use with a fuel dispensing system 14, which is configured to dispense liquid fuel retrieved from fuel storage facility 16 into fuel container 18 via fuel intake line 20, such as the refueling conduit passageway of a vehicle gas tank. Sensor apparatus 10 is preferably configured for integral operation with a vapor recovery system shown generally at 22 and including controller 24 and vapor pump 26, wherein sensor apparatus 10 is operative to implement controllable adjustment of the vapor pump operating speed in accordance with the effluent hydrocarbon concentration detected by sensor apparatus 10, according to a preferred embodiment of the present invention. The gaseous components (i.e., air and hydrocarbon) collected by vapor pump 26 are forwarded to vapor storage 28. The illustrated system is further provided with thermal applicator 30 for applying thermal energy to the sensing elements of fiber-optic sensor apparatus 10 to facilitate removal of hydrocarbon condensate therefrom.

Fuel dispensing system 14 is of conventional construction based upon any one of a variety of dispenser configurations known to those skilled in the art and possessing a general functionality involving the delivery of liquid fuel to a fuel containment reservoir represented by fuel container 18. Accordingly, any particular implementation of fuel dispensing system 14 disclosed herein does not form a part of the present invention and therefore should not serve as a limitation thereof, but instead is set forth herein for illustrative purposes only. Examples of such fuel delivery apparatus may be found in U.S. Pat. Nos. 5,484,000; 5,255,723; 5,345,979; 5,332,008; 5,325,896; 5,323,817; 5,476,125; 5,305,807; 5,507,325; 5,417,256; and U.S. Pat. No. 5,209,275, collectively incorporated herein by reference thereto.

Referring specifically to FIG. 1, fiber-optic sensor apparatus 10 functions broadly as a means to detect the presence of hydrocarbon, generate a certain characteristic form of physical activity in response to such hydrocarbon detection, and couple this generated physical activity to an optical transmission system to preferably produce a reversible deformation in the body of a fiber-based communications medium. The diminished optical transmittance resulting from the fiber microbending is indicative of the concentration of hydrocarbon detected by sensor apparatus 10. The hydrocarbon components subject to detection correspond to the fugitive vapor emissions displaced from fuel container 18 during refueling thereof or as a result of any other condition (e.g., venting) that forces volatilized fuel vapors into the external environment. The variations in optical throughput associated with the detected presence of hydrocarbon are monitored and provided to vapor recovery system 22 for controllable adjustment of the vapor flow rate generated by vapor pump 26 to achieve optimal recovery of the effluent hydrocarbon. The adjustment strategy generally aims to minimize the amount of oxygen subject to collection and delivery to vapor storage 28. For example, at low concentration levels of hydrocarbon indicated by a higher degree of optical transmittance, the vapor collection process will be regulated in such a manner as to reduce the vapor flow rate by decreasing the speed of vapor pump 26.

Referring to FIG. 2, there is shown a schematic block diagram for illustrating a fiber-optic sensor apparatus generally depicted at 40 and corresponding to an implementation of sensor apparatus 10 disclosed in FIG. 1, wherein the absorber-expander element (discussed below) is mechanically coupled to the optical fiber in accordance with one embodiment of the present invention. The illustrated sensor apparatus 40 is preferably configured for placement in the effluent vapor path of a fuel dispensing system. The illustrated sensor apparatus 40 includes an optical transmission system comprising optical fiber 42, laser 44 disposed in light-communicative relationship with fiber 42 at one end thereof for coupling light therein, and optical detector 46 disposed in light-communicative relationship with fiber 42 at another end thereof for detecting light propagating therethrough. The term "light" as used herein refers generally to electromagnetic radiation, which may include, for example, visible radiation or energy outside the visible spectrum (e.g., ultraviolet or infrared), provided that the radiation is capable of transmission via an appropriate communications medium.

Sensor apparatus 40 further includes a sensing structure having an absorber-expander element 48 mechanically coupled to a portion of fiber 42 and characterized by a sensitivity to hydrocarbon in at least one of a liquid state and a vapor state (indicated generally at 50), such that the sensing structure reactively absorbs hydrocarbon upon the presence thereof (i.e., when brought into intimate contact therewith) and expands in response to the absorption activity. It is through this expansion activity that the sensing structure (or an integrally coupled actuator device) engages the fiber body and thereby effectuates the attenuation in light propagation through fiber 42, producing a modulating optical transmittance in fiber 42 that varies in accordance with the presence of hydrocarbon sensed by absorber-expander element 48. As used herein for purposes of brevity, references to sensing structure and absorber-expander element 48 will be used interchangeably.

The sensing structure is characterized such that its response to the presence of hydrocarbon is defined by a property of reversibility, enabling the sensing structure to be repeatedly and substantially restored to an original formation. The restoration process may occur through a variety of hydrocarbon-removal mechanisms, including, but not limited to, diffusion, desorption, and/or evaporation. Thermal applicator 30 (FIG. 1) is provided specifically for this purpose, wherein this heating unit is disposed in a sufficient heat-exchange relationship relative to the absorber-expander element 48 such that thermal energy generated by thermal applicator 30 will be adequately communicated to element 48 to promote the restoration process thereof through hydrocarbon removal. This heat transfer mechanism is particularly useful under operating conditions in which liquid condensate accumulates on the sensing structure, primarily because of the consistent success of the heat exchange process in rapidly evaporating the liquid hydrocarbon, which might otherwise remain if only natural processes were available for the liquid removal. Adequate removal of the hydrocarbon condensate allows the absorber-expander element 48 to undergo a reciprocal contraction cycle that returns element 48 to its original configuration. The reversibility characteristic therefore permits element 48 to experience a virtually hysteresis-free and continuous cycle of hydrocarbon detection and absorption, expansion, hydrocarbon removal, and contraction without any degradation in its structural integrity.

The sensing structure is preferably formed of a material including dimethyl polysiloxane rubber, which is methyl terminated and has silica and iron oxide fillers. This material is commercially distributed under the name of red silicone rubber and is produced commercially by companies such as General Electric Company. It should be apparent to those skilled in the art that conventional processing and shaping techniques are applicable to such a rubber member so as to permit the construction of an absorber-expander element 48 having any desired dimensional characteristics.

The components and subsystems indicated in the embodiments disclosed herein are for illustrative purposes only, as it should be apparent to those skilled in the art that other devices and structures may be substituted therefor to achieve equivalent functionality. For example, fiber 42 may be any communications medium capable of supporting the transmission of light, and may include, for example, a waveguiding medium encompassing such structures as optical fibers, light pipes, and fuzed silica formations, as well as other glass or ceramic structures having suitable light transmission properties. Laser 44 may be any light source or transmitter facility capable of generating and projecting electromagnetic radiation into an appropriate communication s medium. Optical detector 46 may encompass any light detection facility or receiver structure capable of detecting radiation incident thereon and providing a measurement of the intensity level thereof, and which is adaptable for optical coupling to an appropriate communications medium.

Referring to FIG. 3, there is shown a planar cross-sectional view taken in the longitudinal direction along lines A–A' (FIG. 2) for illustrating the physical layout of how absorber-expander element 48 is integrally coupled to optical fiber 42, according to one embodiment of the present invention. As shown, element 48 generally assumes the shape of an elongated cylinder having one longitudinal sect ion thereof being matably oriented in substantial non-deforming abutting engagement with a corresponding longitudinal section of fiber 42. A ring device 52 is preferably provided for retainably and rigidly securing element 48 and fiber 42 in the in dicated arrangement. The expansion activity of element 48 occurring during the presence of hydrocarbon components will cause element 48 to expand, at least in part, into the upper crescent-shaped region circumscribed by ring 52 and create an arcuate-shaped, upwardly-directed microbend in fiber 42 at the point of contact with ring 52. The indicated arrangement, in a preferred form thereof, is precisely configured so that when the absorbed hydrocarbon is removed and element 48 transitions from an expanded state to a fully contracted state, element 48 will return to a static condition (i.e., no hydrocarbon present) characterized by a substantially non-deforming mechanical coupling between element 48 and fiber 42. Otherwise, the arrangement will retain a bias and generate a false indication of hydrocarbon through an unwanted variation in the optical transmittance corresponding to the retained bias. Other such arrangements involving absorber-expander element 48 and fiber 42 encompassed by the present invention are disclosed in U.S. Pat. No. 5,378,889 to Lawrence, incorporated herein by reference and made a part hereof.

As shown in FIG. 2, sensor apparatus 40 is configured for use with vapor pump controller 24, which functions broadly to regulate the collection of vapors by vapor pump 26 in response to and in accordance with the level of effluent hydrocarbon sensed by absorber-expander element 48 and represented by the intensity of light detected by optical detector 46. Integrating sensor apparatus 40 into the indicated vapor recovery system and achieving precise control of the vapor pump flow rate through accurate hydrocarbon detection will preferably require that the sensor apparatus 40 be disposed within the vapor recovery pathway so that the absorber-expander element 48 is exposed for contact with the same hydrocarbon environment as that which is being subjected to the vacuum action of vapor pump 26. Generally, sensor apparatus 40 would have to be suitably placed so as to accommodate accessibility of the hydrocarbon emissions to the sensing structure therein. Proportional control of vapor vacuum action is related to the hydrocarbon amount detected.

Referring specifically to controller 24, an optical converter 25 is provided for converting the level of optical energy detected by optical detector 46 into a vapor control signal representative of the concentration of hydrocarbon sensed by sensor apparatus 40 and represented by the change in transmittance of fiber 42. In particular, the concentration of hydrocarbon is determined as a function of the measured attenuation of the optical throughput in fiber 42. Pump regulator 27 generates a vapor flow signal based on the vapor control signal provided by converter 25, which signifies the change in pump operating speed needed to appropriately adjust the flow rate of pump 26. A means is provided for applying the vapor flow signal to vapor pump 26 to effect control thereof. This methodology of vapor flow regulation is therefore based on hydrocarbon detection by absorber-expander element 48, which generates a motion stimulus (i.e., expansion activity) that is communicated to the vapor recovery system (i.e., pump controller 24) via optical detector 46 as a representative change in optical transmittance.

The physical behavior exhibited by absorber-expander element 48 in response to the presence of hydrocarbon is generally representative of a displacement stimulus that can be easily translated into comparable motion activity through motion transfer devices integrally attached thereto, thereby suggesting other fiber-optic sensor configurations for deformably engaging the optical fiber in addition to the direct mechanical coupling illustrated by FIGS. 2–3. For example, the expansion activity of absorber-expander element 48 may be communicated to an integrally coupled actuator device that itself mechanically engages the fiber via the exertion of a bending influence thereon, thereby altering the fiber transmittance. As discussed below, the present invention encompasses any type of transfer mechanism having the capability of transferring the expansion activity generated by absorber-expander element 48 to the fiber body. It will also become apparent that the attenuation mechanisms may include, but are not limited to, microbending and optical misalignment, such as would occur when plural ones of distinct fiber sections are used to build the communications medium.

FIGS. 4A and 4B are block diagram illustrations of respective fiber-optic sensor apparatus configured for placement in the effluent vapor path of a fuel dispensing system, wherein the absorber-expander element 48 is mechanically coupled to optical fiber 42 via respective coupling devices, according to further embodiments of the present invention. Referring to FIG. 4A, one embodiment of the sensor apparatus includes an absorber-expander element 48 coupled to an actuator 60, which is disposed in expansion-detecting relationship to element 48 and is responsive to the expansion activity thereof for engaging the body of fiber 42. The actuator engagement of the fiber body could, for example, be based on application of a bending stimulus thereto, creating a microbend therein. Referring to FIG. 4B, another embodiment of the sensor apparatus includes an absorber-expander element 48 coupled to an electromechanical transducer 62 (i.e., stress-strain gauge), which is provided to detect the expansion of the sensing structure in response to the presence of hydrocarbon and convert the detected expansion into an electrical signal representative thereof. A fiber coupling element 64 engages the optical fiber in response to and in accordance with the electrical signal provided by electromechanical transducer 62.

In the embodiments described hereinabove, the fiber-optic sensor apparatus was configured to have the fiber-engaging system component (i.e., which directly exerted the microbending stimulus upon the fiber body through intimate contact engagement therebetween) to be mechanically coupled to at least a portion of the fiber body. However, the present invention encompasses other implementations involving fiber-optic sensor apparatus wherein the fiber-engaging device and/or structure is spaced-apart from the optical fiber and becomes sufficiently displaced upon the presence of hydrocarbon (and in response to the expansion activity of the absorber-expander element) to be brought into suitable engagement with the fiber body to produce a microbend therein.

Referring to FIG. 5, there is shown a schematic block diagram for illustrating a fiber-optic sensor apparatus generally depicted at 40 and corresponding to an implementation of sensor apparatus 10 disclosed in FIG. 1, wherein the absorber-expander element 48 is spaced-apart from optical fiber 42 in accordance with another embodiment of the present invention. The illustrated sensor apparatus 40 is identical in all respects to sensor apparatus 40 disclosed in FIG. 2, except that element 48 is displaced from fiber 42 by a separation gap 70 that is maintained during a static condition (i.e., in the absence of hydrocarbon). This orientation is appropriately established so that in the presence of effluent hydrocarbon 50, absorber-expander element 48 sufficiently expands to deformably engage a portion of fiber 42 to produce a microbend therein and induce a change in the transmittance thereof. This spaced-apart orientation is readily configurable utilizing any other embodiment of the fiber-optic sensor apparatus disclosed herein. Referring to FIG. 6, there is shown a planar cross-sectional view taken in the longitudinal direction along lines A–A' (FIG. 5) for illustrating the physical layout of how absorber-expander element 48 is integrally coupled to optical fiber 42 in accordance with the spaced-apart relationship defined therebetween.

In the embodiments described hereinabove, the fiber-optic sensor apparatus was configured with an optical fiber having a continuous, uninterrupted length. However, this illustrative implementation should not serve as a limitation thereof, since the present invention may encompass any suitable fiber-optic communications medium including a plurality of distinct optical fiber sections arranged in seriatim, wherein each fiber section is disposed in light-communicative relationship with any adjacent ones of the plural optical fiber sections and is displaced relative to such adjacent optical fiber sections at free ends thereof by a coupling region therebetween that is light-traversable. The sensing structure may be coupled to any one of the optical fiber sections. Sensor configurations based upon such a sequence of optically coupled fiber sections may implement the variation in optical transmittance by developing a microbend in the fiber, or by using another attenuation mechanism involving an optical misalignment between adjacent fiber sections, which is carried out by effecting a relative transverse displacement between at least one optical fiber section and others of the optical fiber sections adjacent thereto. Additionally, the disclosure in the illustrated embodiments of a single sensing structure for engaging the optical fiber should not serve as a limitation thereof, since the present invention may encompass a plurality of sensing structures disposed in relative spaced-apart relationship along the optical fiber, wherein each sensing structure is coupled to the fiber body by any one of the fiber-engaging configurations disclosed herein (e.g., direct mechanical coupling; indirect coupling via an intermediate coupling element; spaced-apart orientation relative to the fiber body).

Figure 7:
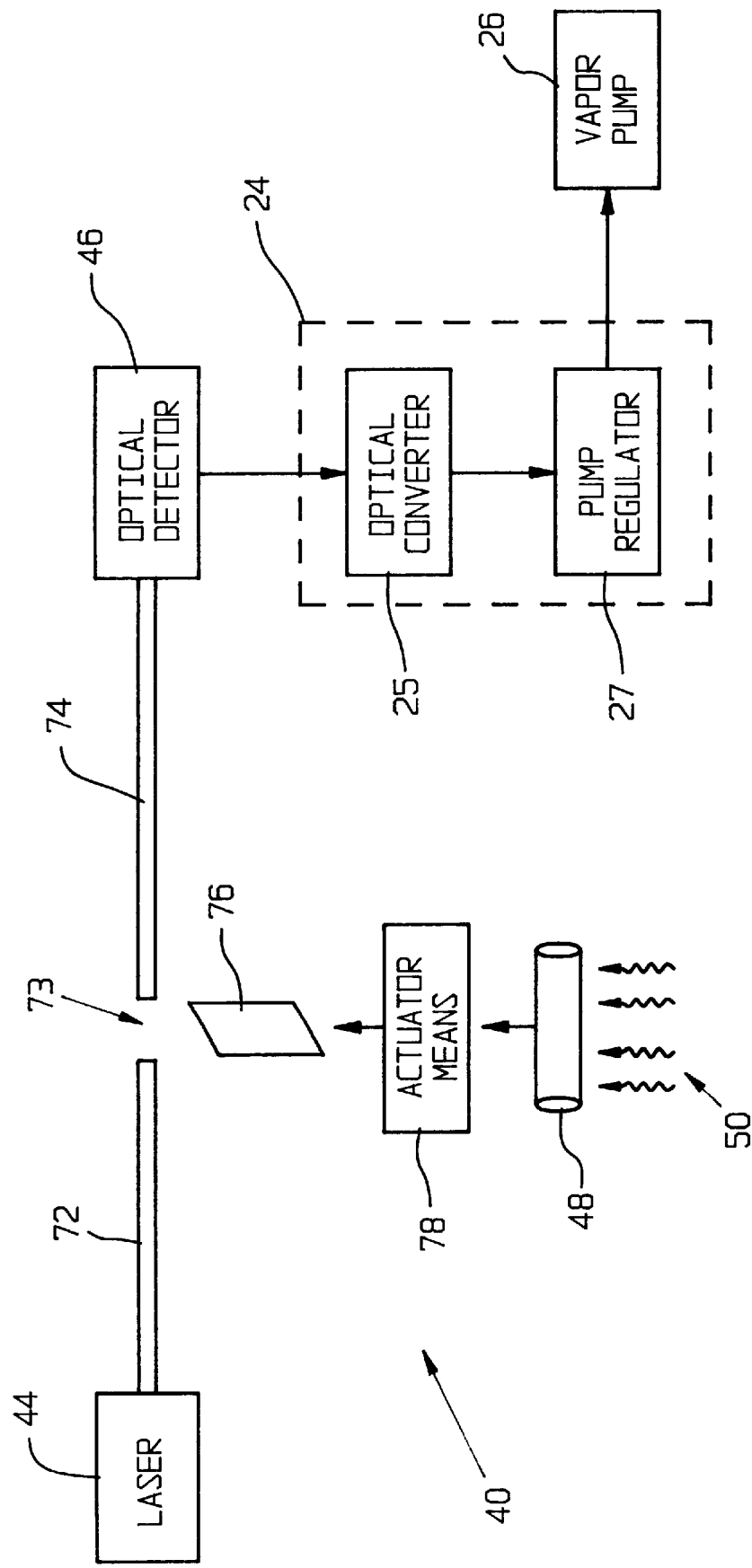
FIG. 7 is a schematic block diagram view of a fiber-optic sensor apparatus configured for placement in the effluent vapor path of a fuel dispensing system, wherein the absorber-expander element actively interposes an integrally attached light-blocking element into the coupling region between two axially aligned fibers upon detecting the presence of hydrocarbon, according to yet another embodiment of the present invention.

Referring to FIG. 7, there is shown a schematic block diagram for illustrating a fiber-optic sensor apparatus generally depicted at 40 and corresponding to an implementation of sensor apparatus 10 disclosed in FIG. 1, wherein the absorber-expander element 48 actively interposes an integrally attached light-blocking element into the coupling region between two axially aligned fibers upon detecting the presence of hydrocarbon, according to yet another embodiment of the present invention. The illustrated sensor apparatus 40 includes a first optical fiber 72 and a second optical fiber 74 disposed in reciprocal light-communicative relationship and relatively displaced at free ends thereof by a coupling region 73 therebetween. A light-blocking element 76 is provided for attenuating the propagation of light incident thereon. There is further provided an actuator means 78 that is integrally coupled to light-blocking element 76 and is disposed relative to absorber-expander element 48 for detection of the expansion activity thereof during the presence of hydrocarbon. Actuator means 78 is operative to sufficiently engage light-blocking element 76 in response to and in accordance with the detected expansion activity of absorber-expander element 48 to reversibly interpose light-blocking element 76 into coupling region 73 to induce a change in the transmittance along the communications channel defined by optical fibers 72 and 74.

The fiber-optic sensor apparatus disclosed herein is particularly suitable for use in a monitoring system for controlling stage II/ORVR interactions, in which it reliably serves as a control mechanism for determining when and to what extent adjustments are needed to correct the vapor pump operating speed, most notably when the sensing structure experiences (i.e., detects) low hydrocarbon concentrations and communicates such a condition as a relatively less-attenuated light signal relative to those corresponding to higher hydrocarbon concentrations.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A system for recovering hydrocarbon effluents from a container for use with a fuel delivery system, comprising:
   communication means for conveying electromagnetic energy;
   transmitter means for introducing electromagnetic energy into said communication means;
   receiver means for detecting electromagnetic energy propagating through said communication means;
   sensor means, disposed in effluent-detecting relationship to said container, for sufficiently engaging said communication means in response to the presence of hydrocarbon effluents sensed by said sensor means to induce a change in the transmittance thereof;
   vapor collection means for controllably collecting the hydrocarbon effluents from said container; and
   regulator means for controlling the rate of effluent collection by said vapor collection means in accordance with the level of energy detected by said receiver means.

2. The system as recited in claim 1, wherein:
   said sensor means is disposed in a vapor recovery pathway.

3. The system as recited in claim 1, further comprises:
   thermal applicator means, disposed in heat-exchange relationship to said sensor means, for applying thermal energy to said sensor means to promote removal of hydrocarbon liquid therefrom.

4. The system as recited in claim 1, wherein:
   said communication means includes an optical fiber;
   said transmitter means includes a light source; and
   said receiver means includes an optical detector.

5. The system as recited in claim 4, wherein the engagement of said communication means by said sensor means effects a microbending of said optical fiber.

6. The system as recited in claim 1, wherein said vapor collection means includes:
   a vapor pump.

7. The system as recited in claim 6, wherein said regulator means further comprises:
   conversion means for converting the energy detected by said receiver means into a vapor control signal representative of the concentration of hydrocarbon sensed by the sensor means and represented by the change in transmittance of said communication means; and
   means for applying the vapor control signal provided by said conversion means to said vapor pump to effect control thereof.

8. The system as recited in claim 1, wherein said communication means includes:
   an optical fiber.

9. The system as recited in claim 8, wherein said sensor means includes:
   a sensing structure, mechanically coupled to at least a portion of said optical fiber and reactively sensitive to the presence of hydrocarbon in at least one of a liquid state and a vapor state, for absorbing hydrocarbon upon the presence thereof and expanding in response thereto.

10. The system as recited in claim 9, wherein the expansion of said sensing structure effects a microbending of said optical fiber.

11. The system as recited in claim 9, wherein said sensing structure is characterized such that the absorption of hydrocarbon therein and the expansion thereof in response to said absorption is repeatedly substantially reversible.

12. The system as recited in claim 9, wherein said sensing structure is formed, at least in part, of a red silicone rubber member.

13. The system as recited in claim 9, further comprises:
    thermal applicator means for controllably applying thermal energy to said sensing structure to promote hydrocarbon desorption therein and effect contraction thereof from a hydrocarbon-induced expansive state.

14. The system as recited in claim 8, wherein said sensor means includes:
    a plurality of sensing structures disposed in relative spaced-apart relationship along said optical fiber and mechanically coupled thereto, each of said plurality of sensing structures being reactively sensitive to the presence of hydrocarbon in at least one of a liquid state and a vapor state for absorbing hydrocarbon upon the presence thereof and expanding in response thereto.

15. The system as recited in claim 1, wherein said communication means includes:
    a plurality of optical fiber sections arranged in seriatim and each disposed in light-communicative relationship with any adjacent ones of said plural optical fiber sections and displaced relative to said adjacent optical fiber sections by a coupling region therebetween.

16. The system as recited in claim 15, wherein said sensor means includes:
    a sensing structure, mechanically coupled to at least a portion of one of said plural optical fiber sections and reactively sensitive to the presence of hydrocarbon in at least one of a liquid state and a vapor state, for absorbing hydrocarbon upon the presence thereof and expanding in response thereto.

17. The system as recited in claim 16, wherein the expansion of said sensing structure effects a microbending of said one optical fiber section.

18. The system as recited in claim 16, wherein the engagement of said communication means by said sensor means effects a relative transverse displacement between said one optical fiber section and others of said optical fiber sections adjacent thereto.

19. The system as recited in claim 16, wherein said sensing structure is characterized such that the absorption of hydrocarbon therein and the expansion thereof in response to said absorption is repeatedly substantially reversible.

20. The system as recited in claim 16, wherein said sensing structure is formed, at least in part, of a red silicone rubber member.

21. The system as recited in claim 16, further comprises:

thermal applicator means for controllably applying thermal energy to said sensing structure to promote hydrocarbon desorption therein and effect contraction thereof from a hydrocarbon-induced expansive state.

22. A system for recovering hydrocarbon effluents from a container for use with a fuel delivery system, comprising:

communication means for conveying electromagnetic energy;

transmission means for introducing electromagnetic energy into said communication means;

receiver means for detecting electromagnetic energy propagating through said communication means;

sensor means, disposed in effluent-sensing relationship to said container and further disposed in spaced-apart relation to said communication means, for engaging said communication means in response to the presence of hydrocarbon effluents sensed by said sensor means to induce a change in the transmittance thereof;

vapor collection means for controllably collecting the hydrocarbon effluents from said container; and regulator means, operatively coupled to said receiver means, for controlling the rate of effluent collection by said vapor collection means in accordance with the level of energy detected by said receiver means.

23. The system as recited in claim 22, wherein:

said sensor means is disposed in a vapor recovery pathway.

24. The system as recited in claim 22, further comprises:

thermal applicator means, disposed in heat-exchange relationship to said sensor means, for applying thermal energy to said sensor means to promote removal of hydrocarbon liquid therefrom.

25. The system as recited in claim 22, wherein:

said communication means includes an optical fiber;

said transmitter means includes a light source; and said receiver means includes an optical detector.

26. The system as recited in claim 22, wherein the engagement of said communication means by said sensor means effects a microbending of said optical fiber.

27. The system as recited in claim 22, wherein said vapor collection means includes:

a vapor pump.

28. The system as recited in claim 27, wherein said regulator means further comprises:

conversion means for converting the energy detected by said receiver means into a vapor control signal representative of the concentration of hydrocarbon sensed by the sensor means and represented by the change in transmittance of said communication means; and means for applying the vapor control signal provided by said conversion means to said vapor pump to effect control thereof.

29. The system as recited in claim 22, wherein said communication means includes:

an optical fiber.

30. The system as recited in claim 29, wherein said sensor means includes:

a sensing structure, disposed in spaced-apart relation to said optical fiber and reactively sensitive to the presence of hydrocarbon in at least one of a liquid state and a vapor state, for absorbing hydrocarbon upon the presence thereof and expanding in response thereto sufficient to bring said sensing structure into engagement with said optical fiber.

31. The system as recited in claim 30, wherein the expansion of said sensing structure effects a microbending of said optical fiber.

32. The system as recited in claim 30, wherein said sensing structure is characterized such that the absorption of hydrocarbon therein and the expansion thereof in response to said absorption is repeatedly substantially reversible.

33. The system as recited in claim 30, wherein said sensing structure is formed, at least in part, of a red silicone rubber member.

34. The system as recited in claim 30, further comprises:

thermal applicator means for controllably applying thermal energy to said sensing structure to promote hydrocarbon desorption therein and effect contraction thereof from a hydrocarbon-induced expansive state.

35. The system as recited in claim 29, wherein said sensor means includes:

a plurality of sensing structures disposed in relative spaced-apart relationship along said optical fiber and each spaced-apart therefrom, each of said plurality of sensing structures being reactively sensitive to the presence of hydrocarbon in at least one of a liquid state and a vapor state for absorbing hydrocarbon upon the presence thereof and expanding in response thereto sufficient to cause at least one of said plurality of sensing structures to be brought into engagement with said optical fiber.

36. The system as recited in claim 29, wherein said sensor means includes:

a sensing structure, reactively sensitive to the presence of hydrocarbon in at least one of a liquid state and a vapor state, for absorbing hydrocarbon upon the presence thereof and expanding in response thereto; and actuator means, disposed relative to said sensing structure for detection of the expansion thereof, for engaging said optical fiber in response to and in accordance with the detected expansion.

37. The system as recited in claim 36, wherein the engagement of said optical fiber by said actuator means effects a microbending of said optical fiber.

38. The system as recited in claim 36, wherein said sensing structure is characterized such that the absorption of hydrocarbon therein and the expansion thereof in response to said absorption is repeatedly substantially reversible.

39. The system as recited in claim 36, wherein said sensing structure is formed, at least in part, of a red silicone rubber member.

40. The system as recited in claim 36, further comprises:

thermal applicator means for controllably applying thermal energy to said sensing structure to promote hydrocarbon desorption therein and effect contraction thereof from a hydrocarbon-induced expansive state.

41. The system as recited in claim 29, wherein said sensor means includes:
   a sensing structure, reactively sensitive to the presence of hydrocarbon in at least one of a liquid state and a vapor state, for absorbing hydrocarbon upon the presence thereof and expanding in response thereto;
   an electromechanical sensor for detecting the expansion of said sensing structure and converting said detected expansion into an electrical signal representative thereof; and
   means for engaging said optical fiber in response to and in accordance with the electrical signal provided by said electromechanical sensor.

42. The system as recited in claim 22, wherein said communication means includes:
   a plurality of optical fiber sections arranged in seriatim and each disposed in light-communicative relationship with any adjacent ones of said plural optical fiber sections and displaced relative to said adjacent optical fiber sections by a coupling region therebetween.

43. The system as recited in claim 42, wherein said sensor means includes:
   a sensing structure, disposed in spaced-apart relation to one of said plural optical fiber sections and reactively sensitive to the presence of hydrocarbon in at least one of a liquid state and a vapor state, for absorbing hydrocarbon upon the presence thereof and expanding in response thereto sufficient to bring said sensing structure into engagement with said one optical fiber section.

44. The system as recited in claim 43, wherein the engagement of said one optical fiber section by said sensing structure during expansion thereof effects a microbending of said one optical fiber section.

45. The system as recited in claim 43, wherein the engagement of said one optical fiber section by said sensing structure during expansion thereof effects a relative transverse displacement between said one optical fiber section and others of said optical fiber sections adjacent thereto.

46. The system as recited in claim 43, wherein said sensing structure is characterized such that the absorption of hydrocarbon therein and the expansion thereof in response to said absorption is repeatedly substantially reversible.

47. The system as recited in claim 43, wherein said sensing structure is formed, at least in part, of a red silicone rubber member.

48. The system as recited in claim 43, further comprises:
   thermal applicator means for controllably applying thermal energy to said sensing structure to promote hydrocarbon desorption therein and effect contraction thereof from a hydrocarbon-induced expansive state.

49. The system as recited in claim 42, wherein said sensor means includes:
   a sensing structure, reactively sensitive to the presence of hydrocarbon in at least one of a liquid state and a vapor state, for absorbing hydrocarbon upon the presence thereof and expanding in response thereto; and
   actuator means, disposed relative to said sensing structure for detection of the expansion thereof, for engaging one of said plural optical fiber sections in response to and in accordance with the detected expansion to induce a change in transmittance of said communication means.

50. The system as recited in claim 49, wherein the engagement of said one optical fiber sections by said actuator means produces a microbend therein.

51. The system as recited in claim 49, wherein the engagement of said one optical fiber section by said actuator means produces an optical misalignment of said one optical fiber section relative to others of said optical fiber sections adjacent thereto.

52. The system as recited in claim 49, wherein said sensing structure is characterized such that the absorption of hydrocarbon therein and the expansion thereof in response to said absorption is repeatedly substantially reversible.

53. The system as recited in claim 49, wherein said sensing structure is formed, at least in part, of a red silicone rubber member.

54. The system as recited in claim 49, further comprises:
   thermal applicator means for controllably applying thermal energy to said sensing structure to promote hydrocarbon desorption therein and effect contraction thereof from a hydrocarbon-induced expansive state.

55. The system as recited in claim 42, wherein said sensor means includes:
   a sensing structure, reactively sensitive to the presence of hydrocarbon in at least one of a liquid state and a vapor state, for absorbing hydrocarbon upon the presence thereof and expanding in response thereto;
   an electromechanical sensor for detecting the expansion of said sensing structure and converting said detected expansion into an electrical signal representative thereof; and
   means for engaging one of said plural optical fiber sections in response to and in accordance with the electrical signal provided by said electromechanical sensor.

56. A system for monitoring the presence of hydrocarbon effluents from a container, said monitoring system being operatively associated with a fuel delivery system operative to dispense fuel into said container, said monitoring system comprising:
   communication means for conveying electromagnetic energy;
   transmitter means for introducing electromagnetic energy into said communication means;
   receiver means for detecting electromagnetic energy propagating through said communication means; and
   sensor means, disposed in effluent-detecting relationship to said container, for sufficiently engaging said communication means in response to the presence of hydrocarbon effluents sensed by said sensor means to induce a change in the transmittance thereof.

57. The system as recited in claim 56, wherein:
   said sensor means is disposed in a vapor recovery pathway.

58. The monitoring system as recited in claim 56, further comprises:
   thermal applicator means, disposed in heat-exchange relationship to said sensor means, for applying thermal energy to said sensor means to promote removal of hydrocarbon liquid therefrom.

59. The monitoring system as recited in claim 56, wherein said communication means includes:
   an optical fiber.

60. The monitoring system as recited in claim 59, wherein said sensor means includes:
   a sensing structure, mechanically coupled to at least a portion of said optical fiber and reactively sensitive to the presence of hydrocarbon in at least one of a liquid state and a vapor state, for absorbing hydrocarbon upon the presence thereof and expanding in response thereto.

61. The monitoring system as recited in claim 60, wherein the expansion of said sensing structure effects a microbending of said optical fiber.

62. The monitoring system as recited in claim 60, wherein said sensing structure is characterized such that the absorption of hydrocarbon therein and the expansion thereof in response to said absorption is repeatedly substantially reversible.

63. The monitoring system as recited in claim 60, wherein said sensing structure is formed, at least in part, of a red silicone rubber member.

64. The monitoring system as recited in claim 60, further comprises:
thermal applicator means for controllably applying thermal energy to said sensing structure to promote hydrocarbon desorption therein and effect contraction thereof from a hydrocarbon-induced expansive state.

65. A system for monitoring the presence of hydrocarbon effluents from a container, said monitoring system being operatively associated with a fuel delivery system operative to dispense fuel into said container, said monitoring system comprising:
a first optical fiber and a second optical fiber disposed in reciprocal light-communicative relationship and relatively displaced at free ends thereof by a coupling region therebetween;
transmitter means for introducing electromagnetic energy into said first optical fiber;
receiver means for detecting electromagnetic energy propagating through said second optical fiber;
a sensing structure, disposed in effluent-detecting relationship to said container and reactively sensitive to the presence of hydrocarbon in at least one of a liquid state and a vapor state, for absorbing hydrocarbon upon the presence thereof and expanding in response thereto;
light-blocking means for attenuating the propagation of light incident thereon; and
actuator means, integrally coupled to said light-blocking means and disposed relative to said sensing structure for detection of the expansion thereof, for sufficiently engaging said light-blocking means in response to and in accordance with the detected expansion to reversibly interpose said light-blocking means into the coupling region between the respective free ends of said first optical fiber and said second optical fiber to induce a change in the transmittance therebetween.

66. The system as recited in claim 65, wherein said sensing structure is characterized such that the absorption of hydrocarbon therein and the expansion thereof in response to said absorption is repeatedly substantially reversible.

67. The system as recited in claim 65, wherein said sensing structure is formed, at least in part, of a red silicone rubber member.

68. The system as recited in claim 65, further comprises:
thermal applicator means for controllably applying thermal energy to said sensing structure to promote hydrocarbon desorption therein and effect contraction thereof from a hydrocarbon-induced expansive state.

69. A method of recovering hydrocarbon effluents from a container for use with a fuel delivery system, comprising the steps of:
providing an optical fiber;
transmitting electromagnetic energy into said optical fiber;
providing a sensing structure, disposed in effluent-detecting relationship to said container, for sufficiently engaging said optical fiber in response to the presence of hydrocarbon effluents sensed by said sensing structure to induce a change in the transmittance thereof;
detecting electromagnetic energy propagating through said optical fiber;
controllably collecting the hydrocarbon effluents from said container; and
regulating the rate of effluent collection in accordance with the level of detected energy.

70. The method as recited in claim 69, wherein said sensing structure is formed, at least in part, of a red silicone rubber member.

71. The method as recited in claim 69, further comprises the step of:
applying thermal energy to said sensing structure to promote removal of hydrocarbon liquid therefrom.

72. The method as recited in claim 69, wherein said sensing structure is reactively sensitive to the presence of hydrocarbon in at least one of a liquid state and a vapor state for absorbing hydrocarbon upon the presence thereof and expanding in response thereto.

73. The method as recited in claim 72, wherein the expansion of said sensing structure effects a microbending of said optical fiber.

74. The method as recited in claim 72, wherein said sensing structure is characterized such that the absorption of hydrocarbon therein and the expansion thereof in response to said absorption is repeatedly substantially reversible.

75. The method as recited in claim 72, further comprises the step of:
applying thermal energy to said sensing structure to promote hydrocarbon desorption therein and effect contraction thereof from a hydrocarbon-induced expansive state.

76. A method of monitoring the presence of hydrocarbon effluents from a container for use with a fuel delivery system operative to dispense fuel into said container, said monitoring method comprising the steps of:
providing an optical fiber;
transmitting electromagnetic energy into said optical fiber;
providing a sensing structure, disposed in effluent-detecting relationship to said container, for sufficiently engaging said optical fiber in response to the presence of hydrocarbon effluents sensed by said sensing structure to induce a change in the transmittance thereof; and
detecting electromagnetic energy propagating through said optical fiber.

77. The method as recited in claim 76, further comprises the steps of:
controllably collecting the hydrocarbon effluents from said container with a vapor pump; and
regulating the rate of effluent collection in accordance with the level of detected energy.

78. The method as recited in claim 76, wherein said sensing structure is formed, at least in part, of a red silicone rubber member.

79. The method as recited in claim 76, further comprises the step of:
applying thermal energy to said sensing structure to promote removal of hydrocarbon liquid therefrom.

80. The method as recited in claim 76, wherein said sensing structure is reactively sensitive to the presence of hydrocarbon in at least one of a liquid state and a vapor state for absorbing hydrocarbon upon the presence thereof and expanding in response thereto.

81. The method as recited in claim 80, wherein the expansion of said sensing structure effects a microbending of said optical fiber.

82. The method as recited in claim 80, wherein said sensing structure is characterized such that the absorption of hydrocarbon therein and the expansion thereof in response to said absorption is repeatedly substantially reversible.

83. The method as recited in claim 80, further comprises the step of:

applying thermal energy to said sensing structure to promote hydrocarbon desorption therein and effect contraction thereof from a hydrocarbon-induced expansive state.

* * * * *